United States Patent [19]

Colpitts et al.

[11] 4,024,636
[45] May 24, 1977

[54] DENTURES

[75] Inventors: Ralph W. Colpitts, St. Louis, Mo.; Kurt C. Frisch, Grosse Ile; Adolfas Damusis, Southfield, both of Mich.

[73] Assignee: Polythetics, Inc., St. Louis, Mo.

[22] Filed: July 11, 1975

[21] Appl. No.: 595,171

[52] U.S. Cl. .................................................. 32/2
[51] Int. Cl.² ....................................... A61C 13/00
[58] Field of Search .................................... 32/2

[56] References Cited
UNITED STATES PATENTS

| | | | |
|---|---|---|---|
| 3,241,238 | 3/1966 | Kersden | 32/2 |
| 3,727,309 | 4/1973 | Huey | 32/2 |

Primary Examiner—Robert Peshock
Attorney, Agent, or Firm—Gordon W. Hueschen

[57] ABSTRACT

A denture consisting of teeth anchored in a gum member composed of a unitary mass of non-hydrophilic polyurethane elastomer, the tooth-holding portion of which is hard and the mouth-engaging portion of which is soft is prepared by first casting the teeth-holding portion about the teeth and then casting the gum holding portion onto the tooth-holding portion and curing the denture during which the gum-engaging portion and the tooth-holding portion become integrally chemically bonded into a unitary mass.

9 Claims, 11 Drawing Figures

DENTURES

BACKGROUND OF INVENTION

1. Field of Invention

This invention relates to novel dentures and to a method of preparing the same. It is particularly directed to novel dentures in which the teeth are anchored in a gum member comprising a tooth-holding portion and a mouth-engaging portion, the tooth-holding portion of which is composed essentially of non-hydrophilic polyurethane elastomer having a hardness of not less than about Shore D 40 and the mouth-engaging portion of which is composed essentially of soft non-hydrophilic polyurethane elastomer having a hardness of not greater than about Shore A 65 integrally chemically bonded together into a unitary mass.

2. Prior Art

It has been proposed to provide dentures with a soft layer in contact with the gums and other mouth parts to provide tissue relief. Such soft layers have been composed of acrylics, silicones, and like rubber-like materials. But on aging, such soft layers tend to harden and give off undesirable odors. In addition, some decomposition of the polymer may also occur presumably due to an oxidation process as well as to pH fluctuations within the mouth.

OBJECTS OF THE INVENTION

It is an object of the invention to overcome difficulties heretofore encountered in the prior art. It is a further object of the invention to provide dentures having a soft gum-engaging portion integrally chemically bonded to a hard tooth-holding portion. It is a further object of the invention to provide an improved process for producing such dentures and to provide dentures which are inexpensive, trouble-free, and easy to keep clean. Further objects will appear as the description proceeds.

BRIEF DESCRIPTION OF THE INVENTION

The invention consists of a denture and a process for making the same. The denture consists of teeth anchored in a gum member comprising a tooth-holding portion and a mouth-engaging portion, the tooth-holding portion of which is composed essentially of hard non-hydrophilic polyurethane elastomer having a hardness of not less than about Shore D 40, and a mouth-engaging portion of which is composed essentially of soft non-hydrophilic polyurethane elastomer having a hardness of not greater than Shore A 65 integrally and chemically bonded into a unitary mass. The denture is prepared from a model assembly furnished by the dentist after a series of dental impressions, bites, and trials with the patient. The model assembly comprises a wax replicate denture mounted on a mouth model which is either provided in one-half of a flask or is mounted in it by the processor. The wax replicate denture and mouth model are coated with a release agent except for the ends of the teeth and the same is then imbedded in the investment material to form a female mold or investment material to form a female mold or investment having a cavity corresponding to the gum portion of the denture. The wax of the wax replicate denture is then removed leaving the teeth embedded in the cavity. The mouth model which is a model of the parts of the mouth to be engaged by the denture is then coated with wax shim and the two halves of the flask assembled together to provide a denture mold. Hard non-hydrophilic polyurethane elastomer-forming material is then introduced into the cavity and allowed or caused to set up therein to form hard non-hydrophilic polyurethane elastomer. The wax shim is then removed and the space vacated by the removal of the wax shim filled with soft non-hydrophilic polyurethane-forming material which is there allowed or caused to set up to form soft non-hydrophilic polyurethane elastomer and to integrally chemically unite with the portions of the hard non-hydrophilic polyurethane elastomer with which it is in contact and thereby to form a unitary mass. Suitable wax sprues are provided at the beginning to provide sprue holes for the introduction of the elastomer-forming material. The cast dentures are then removed from the mold and finished as needed, for example, by removing the sprues and flash and polishing.

For forming the female mold, any suitable investment material may be used. It has been found according to the invention, however, that it is of advantage to use a rigid polyurethane foam-forming material because it is simple to mix up such material, inject it into the mold cavity and allow it to set up therein. It has the advantage of providing light, strong investment which, unlike plaster or investment compound, can be easily broken away from the cast denture and sprues, if necessary, to effect removal of the dentures from the mold. The rigid polyurethane foam also provides a dimensionally stable mold. Any of the so-called one-shot or foam-in-place formulations can be utilized.

Suitable pigments and/or dyes can be incorporated in the polyurethane elastomer-forming material as may be needed to give the desired color to the gums.

Polyurethane elastomers of varying degrees of hardness and elasticity are known in the art. They include both the simple urethane polymers and the urethane copolymers, such as urethane-urea copolymers. Any of these known polyurethane polymers can be utilized for the purposes of this invention provided the components are not colored or at least the resulting product is not colored in such a way that the desired coloring of the gums cannot be obtained by the introduction of pigments and dyes. Also, provided that the elastomers are not hydrophilic and provided they have a degree of hardness consonant with the purposes of the invention. The hard non-hydrophilic polyurethane elastomers should have a hardness of at least Shore D 40 and up to about Shore D 70, whereas the soft non-hydrophilic polyurethane elastomer should not have a hardness greater than about Shore A 65 and preferably at least about Shore A 15. Preferred non-hydrophilic elastomers are those formed by isocyanate-terminated prepolymers which are cross-linked or cured by mixing with a crosslinking agent and heating as required to effect curing.

Isocyanate-terminated prepolymers suitable for preparing the hard non-hydrophilic polyurethane elastomers (hard prepolymers) are prepared by the reaction of polyether diols or triols with aliphatic or cycloaliphatic or aralkyl di- or polyisocyanates in proportion to give free NCO groups. The prepolymers are then cured or cross-linked with a diol, polyol, an alkanolamine, a diamine or a tertiary amine containing polyol, or blends thereof. Advantageously, the diol or polyol is a polyether diol or polyol or a hydroxyl-terminated prepolymer.

The polyether diols can be selected from poly-(oxypropylene glycols, poly-(oxypropylene)poly-(oxyethylene) glycols, poly-(1,4-oxypropylene) glycols, graft copolymers of poly-(oxypropylene)-(polyoxyethylene) glycols with acrylonitrile or mixtures of acrylonitrile and styrene ("Polymer Polyols"). The equivalent weight of these polyether ether diols may range between 200 to 1000 with a preferred range of 200 to 400. The polyol may consist of simple polyfunctional alcohols such as glycerine, trimethylolpropane, 1,2,6-hexanetriol, or pentaerythritol, or they may consist of polyether triols such as poly(oxypropylene) or poly(oxyethylene) adducts of the above polyols. The equivalent weight of the polyether polyols may range between 100 to 800 with a preferred range of 100 to 500. It is also understood that various combinations of diols and polyols may be used.

Isocyanate-terminated prepolymers suitable for preparing the soft polyurethane elastomers (soft prepolymers) are based on polyether diols alone or combinations of polyether diols or triols, and aliphatic, cycloaliphatic or aralkyl di- or polyisocyanates. The same diols and polyols as described above may be used but the average equivalent weight is significantly higher than that used in the preparation of the hard polymer. The preferred range of equivalent weight of the polyethers (diols or combination of diols and triols) is 450 to 1500. They are cured in the same way as the hard prepolymers.

The diisocyanates used for the preparation of the hard or soft isocyanate-terminated prepolymers may be selected from the following, although they are not necessarily restricted to these examples:

4,4'-Dicyclohexylmethane diisocyanate, isophorone diisocyanate, 2,2,4-trimethyl-1,6-hexane diisocyanate, hexamethylene diisocyanate, xylylene diisocyanate, "dimeryl" diisocyanate, methylcyclohexyl diisocyanate and the reaction product of 3 moles of hexamethylene diisocyanate with one mole of water (Desmodur N-triisocyanate).

The ratio of NCO to OH in the preparation of the soft isocyanate-terminated prepolymer may range between 1.75 to 2.5 with a preferred range of 2.0 to 2.25, while the NCO/OH of the hard isocyanate-terminated prepolymer may range between 2 to 3. The soft isocyanate-terminated prepolymers should have a free NCO content of about 3.5 to 5.5 percent, preferably, 3.7 to 4.7 percent, and the hard isocyanate-terminated propolymers, a free NCO content of about 9.5 to 14 percent, preferably, 10 to 13 percent.

For the curing (crosslinking) of the soft or hard prepolymers, preferred polyols are tertiary amine- containing polyols such as poly(oxypropylene) or poly(oxyethylene) adducts of diamines or triamines, such as ethylenediamine, diethylene triamine, tolyenediamine, phenylenediamine, or aniline, or any diols, polyols or their blends. Advantageously, they are polyols of relatively low molecular weight such as are obtained by condensing propylene oxide with ethylenediamine or pentaerythritol to a molecular weight of about 500, or of trimethylolpropane or any other base compound to a molecular weight up to 2500.

Another preferred curing or crosslinking agent is a hydroxyl-terminated prepolymer. These are prepared essentially the same way as the isocyanate-terminated prepolymers but the ratio is such that there are free and un-reacted hydroxyl groups. The same diols and polyol and isocyanates can be used, though it is preferred that the prepolymer have a functionality greater than 2, which can be obtained by using a polyol having a functionality greater than 2 and/or an isocyanate having a functionality greater than 2. Advantageously, the isocyanate is 2,2,4-trimethyl-1,6-hexane diisocyanate, hexamethylene diisocyanate and Desmodur N.

The ratio of OH/NCO in the hydroxyl-terminated prepolymers, advantageously, may be in the same range as the NCO/OH ratio in the isocyanate-terminated prepolymers. It will be understood, however, that inasmuch as the crosslinking agent may consist of one or more diols or polyols (no isocyanate), the ultimate OH/NCO ratio is infinity.

Another preferred curing or crosslinking agent is a prepolymer-polyol blend. Thus, a polyurethane prepolymer, advantageously, one having neither free NCO nor free OH groups, can be mixed with a polyol, advantageously a polyol having a functionality of more than 2, to form a prepolymer-polyol blend. When such a blend is mixed with an isocyanate-terminated prepolymer in a NCO/OH ratio of greater than 1, crosslinking is effected both through an NCO-OH reaction and through NCO-urethane reaction.

The isocyanate-terminated prepolymers and the crosslinking agent should be mixed together in proportions to give an NCO/OH ratio of at least about 1.05 to 1.0 and preferably not greater than 1.1 to 1.0. This excess of NCO groups ensures a crosslinked polymer which is non-hydrophilic and one which is sufficiently reactive so that the soft non-hydrophilic polyurethane elastomers react chemically with the hard non-hydrophilic polyurethane elastomers to form an integral and unitary chemical bond between the two.

In order to accelerate the formation of the prepolymers or the cure of both the hard and soft isocyanate-terminated prepolymers with the crosslinking agents, metal catalysts such as tin catalysts, for example, dibutyltin dilaurate and stannous octanoate can be used.

DETAILED DESCRIPTION OF THE INVENTION

Figure 1:
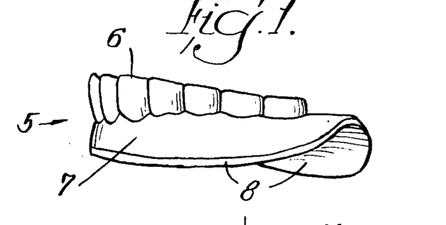
FIG. 1 is a side elevation of a denture according to the invention.
Figure 2:
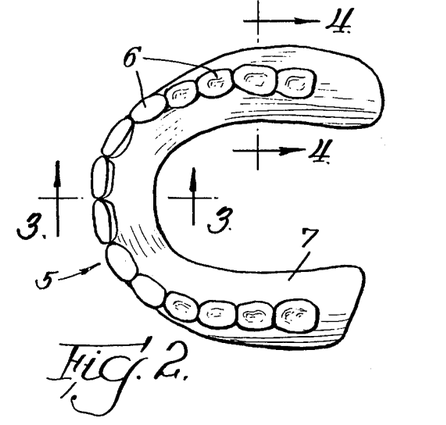
FIG. 2 is a plan view of FIG. 1

As shown in the side elevation of FIG. 1 and in plan view in FIG. 2, 5 represents a denture according to the invention, 6 the artificial teeth, and 7 the artificial gums in which teeth 6 are imbedded. The tooth-holding portion of the gums are composed of hard polyurethane elastomer and the mouth-engaging portion 8, of soft polyurethane elastomer. The hard portion 7 and the soft portion 8 are unitarily and integrally united by a chemical bond which results when the mouth-engaging portion is cast in contact with the tooth-holding portion.

Figure 3:
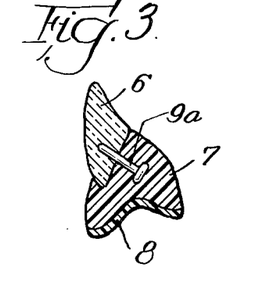
FIG. 3 is a cross-section taken along lines 3—3 of FIG. 2.
Figure 4:
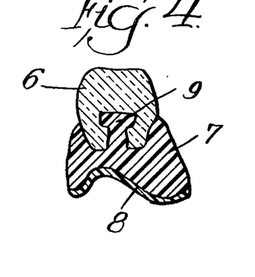
FIG. 4 is a cross-section taken along lines 4—4 of FIG. 2.

FIG. 3 shows a cross-section of the anterior portion with the anterior teeth 6 imbedded in the tooth-holding portion 7 and anchored therein by pins 9a. FIG. 4 shows a cross-section of the posterior portion with the posterior teeth 6 anchored in the tooth-holding portion 7 by means of the diotoric 9, that is, a T-shaped channel or undercut hole.

Figure 5:
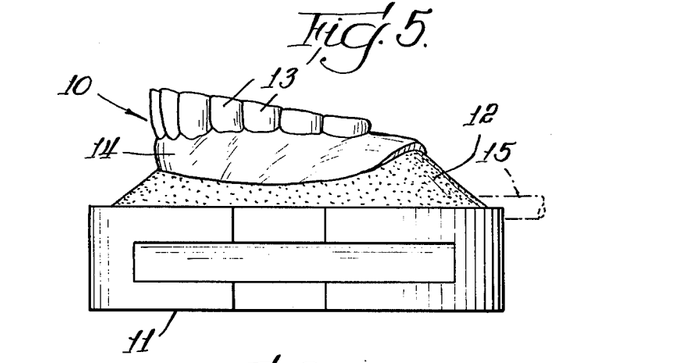
FIG. 5 is a side elevation of the mouth model with replicate denture thereon.
Figure 6:
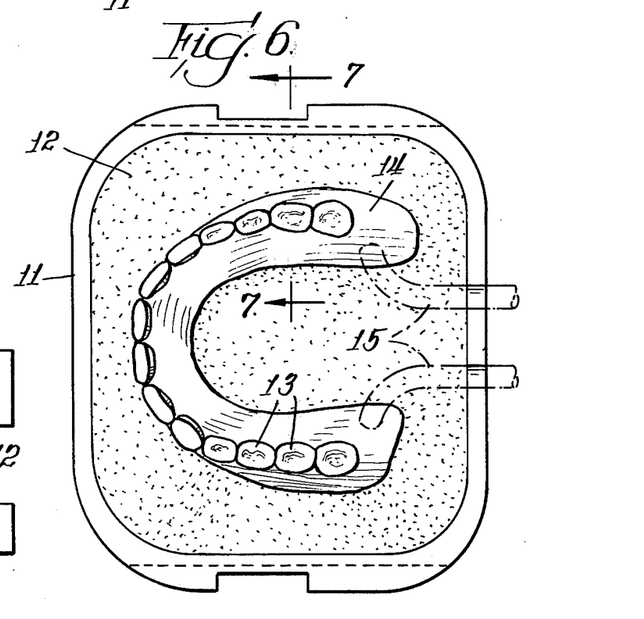
FIG. 6 is a plan view of FIG. 5.
Figure 7:
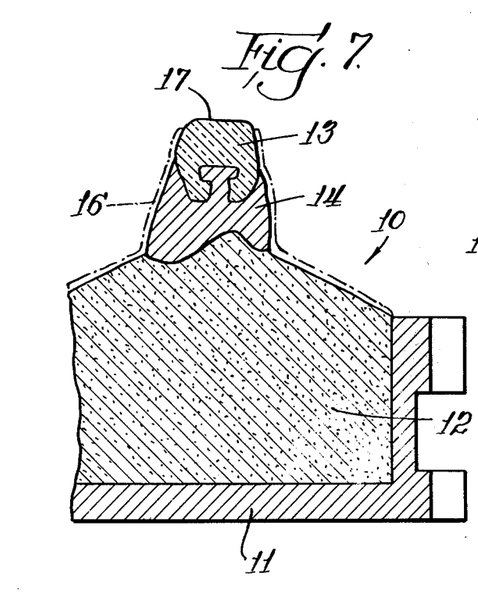
FIG. 7 is a cross-section taken along lines 7—7 of FIG. 6.

By the techniques of this invention, the denture 5 has the shape and configuration of the wax replicate denture 10 prepared by the dentist or dental technician. The wax replicate denture 10 includes a wax pattern 14, or gum portion, with the teeth 13 imbedded therein. The wax replicate denture 10 is positioned on the mouth model 12 and the whole constituting the model assembly is mounted in the upper half 11 of the flask 21. This model assembly is prepared in the usual manner after a series of dental impressions, bites, and trials with the patient so that the wax replicate denture represents exactly what the dentist wants the final dentures to be like.

Figure 8:
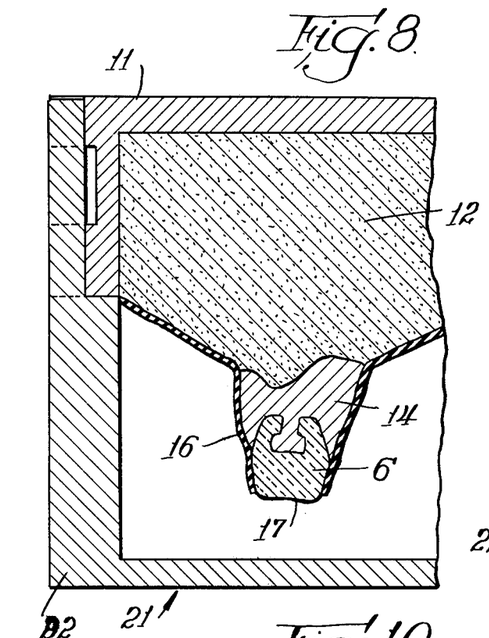
FIG. 8 is a cross-section of the assembled flask.

In preparing dentures from the model assembly, there is attached to the inner ends of the posterior portions of the wax pattern 14, wax sprues 15 for the purpose of providing sprue holes into the mold cavity. These wax sprues should lie on, or be partially imbedded in the edges of the mouth model. (By edges of the mouth model is meant the portions extending beyond the actual impression of the gums or palate), and so shaped and so located that when the mouth model is removed for the investment mold, yet to be described, the cast denture and sprues can be easily removed. The entire exposed surface of the model assembly is then coated with a coating 16 of release material, except for the ends 17 of the teeth, and the whole assembly inserted into the bottom half 22 of the flask 21 as shown in FIG. 8. The bottom half of the flask is then filled with investment material 23 which is allowed to or caused to set up. On removal of the model assembly, the teeth 6 are left in the mold or investment cavity 24 which conforms to the shape of the wax replicate denture 10. Some wax may also remain but this can be easily removed by washing with hot water or by boiling it off.

Figure 9:
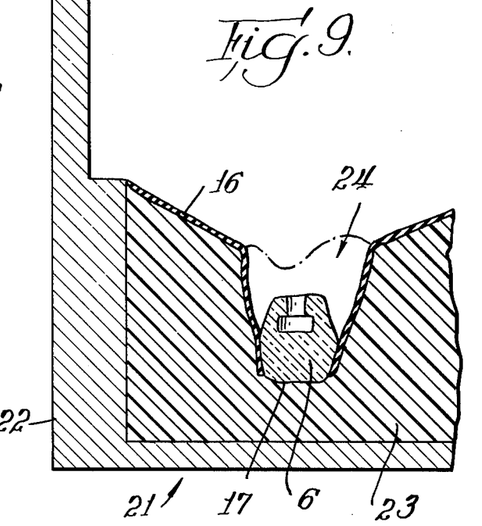
FIG. 9 is a cross-section of the lower investment or female mold showing the teeth in place.
Figure 10:
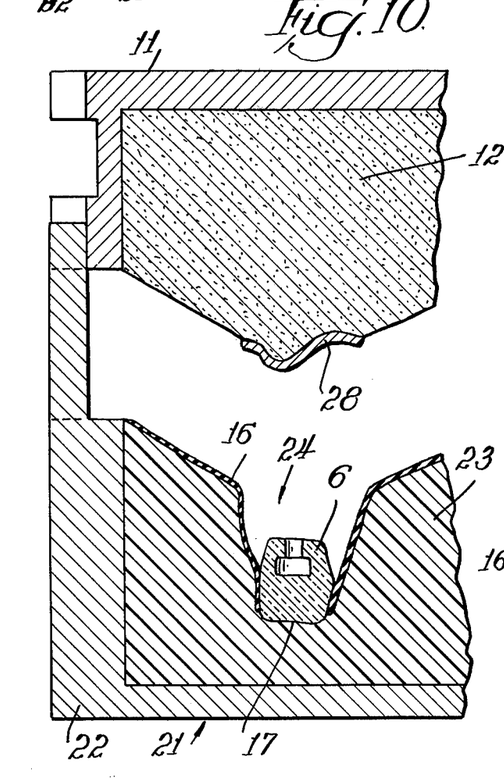
FIG. 10 is an expanded view in cross-section showing the mouth model and wax shim being placed on top of the investment of female mold.
Figure 11:
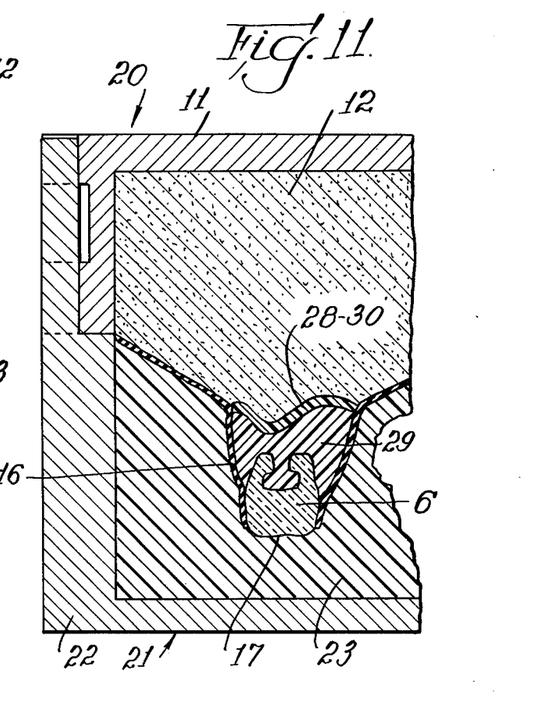
FIG. 11 is a cross-section of the assembled flask showing the cast denture therein.

The cavity 24 now forms the mold with the teeth in place ready for the filling with hard non-hydrophilic polyurethane elastomer-forming material. Before this, however, the last vestiges of wax are removed from the mouth model and a wax shim 28 applied to the mouth-engaging parts. The wax shim 28 should have substantial thickness according to the thickness desired for the soft gum-engaging portion of the dentures. It may, for example, be about 1 to 5 millimeters thick. The upper part 11 of the flask is now inverted and placed on the lower part 22 as shown in FIG. 10 and the two are clamped together to form the first denture mold. Hard non-hydrophilic polyurethane elastomer-forming material is then introduced into the mold through suitable sprue holes previously made by the wax sprues 15, one of which serves for introducing the material and the other of which serves to vent the cavity. The material is then caused to set up on the mold until at least a partial cure is obtained and there is thus obtained the hard tooth-holding portion 29 shown in FIG. 11. The wax shim 28 is now removed in the usual manner of washing with hot water or boiling off, either with or without separation of the flask and soft non-hydrophilic polyurethane elastomer-forming material introduced through the same sprue holes and caused to set up therein to form the soft gum-engaging portion 30 shown in FIG. 11. The cure is effected by heating during which there is a chemical interaction between the hard elastomer 29 and the soft elastomer 30 due to the interaction of the free NCO groups with the polyurethane linkages. Thus, the isocyanate groups of the soft elastomer react with urethane linkages of the hard elastomer and vice versa to provide a unitary mass in which the hard and soft elastomers are integrally chemically united and in which no seam or juncture is discernable. The flasks are separated and the denture removed and finished by removing flash and sprues and polishing as needed. Though the ends of the teeth 17 were not coated with release material, they break free readily from the investment material.

It will be understood that the release material 16 and 16a is not actually as thick as shown since it is really nothing more than a coating of latex, silicone, shellac, zinc stearate, or the like.

The investment material, advantageously, is a rigid polyurethane foam such as commonly used for insulation purposes. Two-component systems are readily available on the market which in a short time after mixing, will set up into a rigid blown foam. It is sufficient simply to mix the two components together and to inject a measured quantity into the mold cavity through suitable sprue holes, where in a few minutes or a few seconds, according to the time factor of the particular composition, it will begin to foam and will fill up the bottom half of the flask 21 into close and intimate contact with the model assembly therein. A hole, or holes, may be provided in a wall to the lower half of the flask to vent the flask and to provide for expansion in case too much of the foam-forming material is introduced into the flask cavity. The flask is placed in a suitable clamp (not shown), to assure that any pressure engendered by the blowing of the foam or any of the subsequent operations, will not disrupt the relative position of the upper and lower flasks. The size of the sprue holes and the vents can be adjusted to the amount of material introduced to cause more or less pressure to be exerted as the foam sets up.

In contradistinction, the non-hydrophilic polyurethane elastomer-forming compositions or materials of the invention do not set up spontaneously and do not expand on setting up. Nonetheless, the flask should be tightly clamped to insure that a precise replication is obtained. The isocyanate-terminated polymers used in the invention are liquids or heat-liquefiable materials as are the crosslinking agents. When the two are mixed in the proper proportions at the proper temperature, the resulting liquid can be poured into or injected into the molds as required and there caused to set up by holding at a suitable temperature for a requisite period according to the time constant and cure constant of the particular system used. Suitable such systems are illustrated in the following Formulations and Examples in which the parts and percentages are by weight unless otherwise specified.

I — SOFT ISOCYANATE-TERMINATED PREPOLYMERS
(Components A)
FORMULATION 1

Polymeg 1000[1], 4 moles × 976 = 3904

I — SOFT ISOCYANATE-TERMINATED PREPOLYMERS
(Components A)
FORMULATION 1

| | |
|---|---|
| Polymeg 2000[2], 1 mole × 1998 | = 1998 |
| Hylene W[3], 10 moles × 262 | = 2620 |
| Dibutyltin dilaurate catalyst | 1.7 |
| | 8523.7 |
| Equivalent weight per one NCO | 852.4 |

[1]Poly(oxytetramethylene) glycol; Mol. wt. 976
[2]Poly(oxytetramethylene) glycol; Mol. wt. 1998
[3]4,4'-dicyclohexylmethane diisocyanate

PREPARATION PROCEDURE

Polymeg 1000 and Polymeg 2000 are charged into the reactor and the mixture heated to 70° C. It is demoisturized in vacuum for 2–3 hours until the evolution of bubbles ceases.

Afterwards a dry nitrogen blanket is applied and the mixture is cooled to 50° C and Hylene is added. The reaction mixture is stirred at 100–120 rpm for at least 30 minutes and watched, for a slight exothermic reaction may ensue. The temperature of the reactor is maintained at 65–70° C. The catalyst is added in portions in order to speed up the reaction. After 3 hours have elapsed the NCO content is checked using the n-dibutylamine titration method. The NCO content should be in the range of 4.8%. The variation here and elsewhere may be ±5 percent.

When this level of free NCO is reached, the contents of the reactor are cooled and are packaged into 1 gallon or 1 quart lined containers. Dry nitrogen is used to maintain an inert atmosphere in the containers which are then tightly closed.

FORMULATION 2

| | |
|---|---|
| Polymeg 1000, 2 moles × 976 | = 1952 |
| Polymeg 2000, 1 mole × 1998 | = 1998 |
| Hylene W, 6 moles × 262 | = 1572 |
| Dibutyltin dilaurate catalyst | 1.1 |
| | 5523.1 |
| Equivalent weight per one NCO | 920.5 |

Preparation procedures are the same as in Formulation 1. The free NCO content of the prepolymer should be 4.56%.

FORMULATION 3

| | |
|---|---|
| Polymeg 2000, 1 mole × 1998 | = 1998 |
| Polymeg 1000, 1 mole × 976 | = 976 |
| Hylene W, 4 moles × 262 | = 1048 |
| | 4022 |
| Equivalent weight per one NCO | 1005.5 |

Preparation procedures are the same as in Formulation 1. The free NCO content should be 4.18%.

FORMULATION 4

| | |
|---|---|
| Polymeg 2000 | 1198 |
| Polymeg 1000 | 488 |
| Hylene W | 786 |
| Dibutyltin dilaurate, catalyst | .76 |
| | 3272.76 |
| Equivalent weight per one NCO | 1190 |

PREPARATION PROCEDURE

Poly (oxytetramethylene) glycols, Polymeg 2000 and Polymeg 1000, are charged into a reactor and demoisturized in vacuum for 2–3 hours upon a gentle stirring of 60–120 rpm at 70° C.

The demoisturized glycol mixture is cooled down to 50° C, a dry nitrogen blanket is applied, and diisocyanate (Hylene W) is added. The catalyst is added in portions in order to speed up the reaction.

The charge of the reactor should exotherm. The temperature of the reactants should not be allowed to go over 75° C. After 2–3 hours of the reaction, the NCO content should be checked by the n-dibutylamine titration method. The NCO content should be in the range of 3.3%. If the content of NCO higher than 3.7% is found, the heating should be continued for an additional hour at 70° C after the addition of a small amount (0.005%) of the catalyst.

The above soft isocyanate-terminated prepolymers are essentially linear.

II — HARD ISOCYANATE-TERMINATED PREPOLYMERS
(Components A)
FORMULATION 5

| | |
|---|---|
| Polymeg 650[1], 1 mole | = 650 |
| Pluracol TP 440[2], 1 mole | = 420 |
| Hylene W[3], 7 moles | = 1834 |
| Dibutyltin dilaurate catalyst | 0.6 |
| | 2904.6 |
| Equivalent weight per NCO | 322.7 |

[1]Poly(oxytetramethylene) glycol; Mol. wt. 650
[2]Poly(oxypropylene) derivative of trimethylolpropane, Mol. wt. 420
[3]4,4'-dicyclohexylmethane diisocyanate

PREPARATION PROCEDURE

Polymeg 650 and Pluracol TP 440 are charged into the reactor and the mixture is heated to 70° C. It is then demoisturized under vacuum for 2–3 hours until the evolution of bubbles ceases. Afterwards a dry nitrogen blanket is applied, the mixture cooled to 40° C and Hylene W added. The reaction mixture is stirred at 100–200 rpm for at least 30 minutes, taking care to control any exothermic reaction which may occur. The temperature in the reactor is kept at a level of 65–70° C. The catalyst is added in portions, if necessary, to speed up the reaction.

After two hours have elapsed, the NCO content is checked by means of the n-dibutylamine titration method. The NCO content should be in the range of 13%. When this level of free NCO is reached, the contents of the reactor are cooled and packaged into one gallon or one quart lined containers. The empty space in the containers is filled with dry nitrogen.

FORMULATION 6

| | |
|---|---|
| Polymeg 650[1], 2 moles × 650 | = 1300 |
| Pluracol TP 740[2], 1 mole × 720 | = 720 |
| Hylene W, 9 moles | = 2358 |
| Dibutyltin dilaurate catalyst | 0.9 |
| | 4378.9 |
| Equivalent weight per one NCO | 398.0 |

[1]Poly(oxytetramethylene) glycol; Mol. Wt. 650
[2]Poly(oxypropylene) derivative of trimethylolpropane, Mol. wt. 720

Preparation procedure is identical to the Formulation 5 procedure. The free NCO content should be 10.55%.

The above hard isocyanate-terminated prepolymer which is made from a tri-functional polyol is branched and is introduced for crosslinking purposes.

III — CROSSLINKING AGENTS (Components B)
A. For Soft and Hard Elastomer
FORMULATION 7

| | | |
|---|---|---|
| Pluracol 355* | 100 | g. |
| TiO$_2$ (rutile) | 0.2 | g. |
| Yellow No. 6 Lake | 0.04 | g. |
| Red No. 3 Lake | 0.02 | g. |
| Dibutyltin dilaurate catalyst | as needed | |
| Equivalent weight per one hydroxyl | 125.1 | |

*Poly(oxypropylene) derivative of ethylenediamine, Mol. wt. 490

PREPARATION PROCEDURE

All the pigments are dispersed in 5% of the total polyol, Pluracol 355. For dispersion purposes a ball mill or roller mill or any well-dispersing high speed mill can be employed.

Then all of the remainder of the polyol, Pluracol 355, is stirred in. Afterwards the mixture is degassed and demoisturized by applying a vacuum and gentle heating at 60–70° C.

The catalyst has to be added before application. The amount of the catalyst depends on the type of isocyanate-terminated prepolymer to be used. Usually 0.15–0.35% of the catalyst is added, based on the total weight of the polymer and on the type of the polymer and the reacting groups.

FORMULATION 8

| | |
|---|---|
| 1,4-Butanediol | 450 |
| Pluracol PeP 550* | 500 |
| TiO$_2$ | 1. g. |
| Yellow No. 6. Lake | 0.2 g. |
| Red No. 3 Lake | 0.1 |
| Pink No. 1 Lake | 0.005 |
| Dibutyltin dilaurate catalyst | as needed |
| | 951.305 |
| Equivalent weight per one hydroxyl | 68.0 |

*Poly(oxypropylene) adduct of pentaerythritol of about 500 molecular weight

PREPARATION PROCEDURE

All the pigments are dispersed in 5% of the polyols; then all the remainder of the polyols is blended with the pigment dispersion. Afterwards the mixture is demoisturized by applying a vacuum and gentle heating at 60–70° C.

The catalyst has to be added before application. The amount of the catalyst depends of the type of isocyanate-terminated prepolymer to be used.

Usually for the rigid elastomer formulation the amount of the catalyst is in the range of 0.15–0.25%, for the soft elastomer formulation, in the range of 0.30–0.35%.

FORMULATION 9

| | | |
|---|---|---|
| Pluracol Pep 550 | 500 | g. |
| TiO$_2$ | 0.5 | |
| Yellow No. 6 Lake | 0.1 | |
| Red No. 3 Lake | 0.05 | |
| | 500.65 | |
| Equivalent weight per one hydroxyl | 125.1 | |

Preparation procedure is similar to the procedure of Formulation 8.

FORMULATION 10

| | | |
|---|---|---|
| Pluracol TP 440 | 420 | g. |
| Butanediol | 450 | g. |
| TiO$_2$ | 1 | g. |
| Yellow No. 6 Lake | 0.2 | g. |
| Red No. 3 Lake | 0.1 | g. |
| Pink No. 1 Lake | 0.005 | g. |
| Dibutyltin dilaurate catalyst | as needed | |
| | 871.305 | |
| Equivalent weight per one hydroxyl | 67 | |

Preparation procedure is similar to the procedure of Formulation 8.

B. For the Soft Elastomer
FORMULATION 11

| | |
|---|---|
| Desmodur N - triisocyanate[1] | 478 |
| Polymeg 650 | 2112 |
| Pluracol TP 1540[2] | 750 |
| TiO$_2$ | 5.0 |
| Yellow No. 6 Lake | 3.0 |
| Red No. 3 Lake | 1.8 |
| Blue No. 1 Lake | 0.2 |
| | 3350.0 |
| Equivalent weight per one hydroxyl | 668 |

[1] (three moles of hexamethylene diisocyanate reacted with one mole of water)
[2] Poly(oxypropylene) derivative of trimethylolpropane, Mol. Weight 1500

PREPARATION PROCEDURE

Poly(oxytetramethylene) glycol is charged into a reactor and demoisturized in vacuum for 2–3 hours upon gentle stirring at 60–120 rpm at 70° C. Then the vacuum is released under dry nitrogen, and the dry nitrogen blanket is retained during the reaction time.

Desmodur N-triisocyanate is stirred in and reacted with the glycol until the NCO content is reduced to zero. Then Pluracol TP 1540 is blended in.

The pigments are dispersed in a small amount of the triol, Pluracol TP 1540, and stirred in with the total content of the prepolymer-polyol blend.

C. For the Hard Elastomer
FORMULATION 12

| | |
|---|---|
| Desmodur N - triisocyanate | 526 |
| Polymeg 650 | 2,324 |
| Pluracol PeP 650* | 17,150 |
| TiO$_2$, rutile | 40 |
| Yellow No. 6 Base | 24 |
| Red No. 3 Base | 16 |
| Blue No. 1 Base | 2 |
| | 20,082 |
| Equivalent weight per one hydroxyl | 186. |

*Poly(oxypropylene) derivative of pentaerythritol, Mol. Weight ca 600

PREPARATION PROCEDURE

Poly(oxytetramethylene) glycol is charged into a reactor and demoisturized in vacuum for 2–3 hours upon a gentle stirring of 60–120 rpm at 70° C. Then under a dry nitrogen blanket, the triisocyanate is stirred in. The components are reacted until all free NCO disappears. Then Pluracol PeP 650 is blended in. A small portion of Pluracol PeP 650 is employed for dispersion of pigments.

The dispersed pigment base is added to the prepolymer-polyol blend and the contents are stirred properly.

The components A and B are mixed together with the catalyst, degassed and then cast as above described, according to whether the components are selected to produce a hard non-hydrophilic polyurethane elastomer or a soft one. The following examples are illustrative.

EXAMPLE 1

Hard Elastomer

Component A, Formulation 5, 100 parts
Component B, Formulation 7, 36 parts
Catalyst, dibutyltin dilaurate, 8 drops
NCO/OH = 1.08 to 1

Components A and B are degassed and demoisturized for at least one hour at 60° C and then blended gently with the catalyst and placed in a pre-heated vacuum oven for 1–2 minutes. The mixture is then poured into a pre-heated denture mold treated with a mold release material as previously described and heated at 40° C for at least ½–1 hour. A further period of 2 or 3 hours at the same temperature is necessary to achieve a satisfactory cure but this further heating may be effected simultaneously with the curing of the soft elastomer. The two halves of the flask prepared as above described form the complete denture mold, for the casting of the soft-non-hydrophilic polyurethane elastomer onto the cast hard-non-hydrophilic polyurethane elastomer.

The preparation of soft, non-hydrophilic polyurethane elastomers is illustrated in the following example.

EXAMPLE 2

Soft Elastomer

Component A, Formulation 1, 100 parts
Component B, Formulation 7, 13.6 parts
Catalyst, stannous octoate, 8 drops
NCO/OH = 1.08 to 1

Components A and B are degassed and demoisturized for at least 1 hour at 60° C and then blended gently with the catalyst and placed in a pre-heated vacuum oven for 1–2 minutes. They are then cast into a pre-heated denture mold containing a previously cast hard-non-hydrophylic polyurethane elastomer as above described and kept in an oven at 90° C for 3 hours. The denture is then removed from the mold and finished by removing the sprues and flash and polishing as necessary.

In place of the hard non-hydrophilic polyurethane elastomer-forming composition of Example 1, there may be substituted the following.

EXAMPLE 3

Component A, Formulation 5, 100 parts
Component B, Formulation 9, 36.9 parts
Catalyst, dibutyltin dilaurate, 16 drops
NCO/OH = 1.05 to 1

EXAMPLE 4

Component A, Formulation 6, 100 parts
Component B, Formulation 9, 16 parts
Catalyst, dibutyltin dilaurate, 16 drops
NCO/OH =1.05 to 1

The compositions of Examples 3 and 4 are degassed, demoisturized, blended and otherwise treated as in Example 1.

EXAMPLE 5

Hard Elastomer

Component A, Formulation 5, 100 parts
Component B, Formulation 12, 50 parts
Catalyst, stannous octoate, 0.40 parts
NCO/OH = 1.1 to 1

PREPARATION PROCEDURE

Components A and B should be degassed and demoisturized under vacuum before blending. Then the catalyst should be blended in. The charge should be cast into a preheated mold, treated with a mold release agent. The elastomer should be cured for a half hour at 40° C.

The soft non-hydrophilic polyurethane elastomer forming compositions of Example 2 may be substituted by the following:

EXAMPLE 6

Component A, Formulation 2, 100 parts
Components B, Formulation 8, 7 parts
Catalyst, dibutyltin dilaurate, 12 drops
NCO/OH = 1.05 to 1

EXAMPLE 7

Component A, Formulation 3, 100 parts
Component B, Formulation 8, 6.44 parts
Catalyst, dibutyltin dilaurate, 16 drops
NCO/OH = 1.05 to 1.

The compositions of Examples 6 and 7 are degassed, demoisturized, blended, cast, and cured as in Example 2.

EXAMPLE 8

Component A, Formulation 4, 100 parts
Component B, Formulation 11, 56.2 parts
Catalyst, stannous octoate, 0.32
NCO/OH = 1.05 to 1.

PREPARATION PROCEDURE components A and B should be heated up to approximately 60° C and degassed and demoisturized under vacuum before blending. Then the catalyst should be added. The blend should be cast into a preheated mold and heated with a mold release agent. The elastomer should be cured in an oven at 95° C for 2 hours.

Dentures may be made up of any combination of hard non-hydrophilic polyurethane elastomer-forming compositions, for example, Examples 1, 3, 4, and 5 with any of the soft hydrophilic polyurethane elastomer-forming compositions, for example, Examples 2, 5, 6, and 8. Particularly good results are obtained by casting Example 8 on Example 5.

It is to be understood that the invention is not to be limited to the exact details of operation or structure shown and described as obvious modifications and equivalents will be apparent to one skilled in the art.

We claim:

1. A denture consisting of teeth anchored in a gum member comprising a tooth-holding portion and a mouth-engaging portion, the tooth-holding portion being composed essentially of hard non-hydrophilic polyurethane elastomer having a hardness of not less than about Shore D 40, and the mouth engaging portion being composed essentially of soft non-hydrophilic polyurethane elastomer having a hardness of not greater than about Shore A 65, said tooth-holding portion and said mouth-engaging portion being integrally chemically bonded into a unitary mass.

2. The denture of claim 1, in which the hard non-hydrophilic polyurethane elastomer teeth have a hardness of not greater than Shore D 70 and the soft non-hydrophilic polyurethane elastomer gum member has a hardness of not less than about Shore D 15.

3. A denture consisting of teeth anchored in a gum member comprising a tooth-holding portion and a mouth-engaging portion, the tooth-holding portion being composed essentially of hard non-hydrophilic polyurethane elastomer having a hardness of not less than about Shore D 40, and the mouth-engaging portion being composed essentially of soft non-hydrophilic polyurethane elastomer having a hardness of not greater than about Shore A 65, said tooth-holding portion and said mouth-engaging portion being integrally chemically bonded into a unitary mass and in which the hard and soft polyurethane elastomers are cross-linked hard and soft isocyanate-terminated prepolymers, respectively, and have a NCO/OH ratio of about 1.05 to 1.0 to 1.1 to 1.0.

4. The denture of claim 3, in which the soft prepolymer is essentially linear, and the hard prepolymer is branched.

5. The denture of claim 4, in which the soft prepolymer has a free NCO content between about 3.7 and about 5.5 percent and the hard prepolymer has a free NCO content between about 9.5 and about 14 percent.

6. The denture of claim 5, in which the polyol component of the soft prepolymer is poly(oxytetramethylene glycol, the polyol component of the hard prepolymer is a mixture of poly(oxytetramethylene) glycol and the poly(oxypropyl-derivative of trimethylolpropane and the isocyanate component is 4,4-dicyclohexylmethane diisocyanate.

7. The denture of claim 6, in which the cross-linking agent is poly(oxypropylene derivative of ethylene diamine having a molecular weight of about 490.

8. The denture of claim 6, in which the crosslinking agent is poly(oxypropylene) adduct of pentaerythritol of about 500 molecular weight.

9. The denture of claim 6, in which the cross-linking agent is a polyurethane prepolymer-polyol blend in which the prepolymer has neither free NCO nor free hydroxyl groups and the polyol is a polyether polyol having a functionality more than 2.

* * * * *

UNITED STATES PATENT AND TRADEMARK OFFICE
CERTIFICATE OF CORRECTION

PATENT NO. : 4,024,636
DATED : May 24, 1977
INVENTOR(S) : Ralph W. Colpitts, Kurt C. Frisch, Adolfas Damusis It is certified that error appears in the above-identified patent and that said Letters Patent are hereby corrected as shown below:

[56] 1st ref.; should read ---Kersten---
Fig. 8 of drawing; the number 22 in the lower left corner is unreadable in the patent.
Col. 1, Line 61-62; "investment material to form a female mold or investment material to form a female mold or investment having a" should read ---investment material to form a female mold or investment having a ---
Col. 3, Line 5; "polyether ether diols" should read ---polyether diols---
Col. 3, Line 46-47; "propolymers" should read ---prepolymers---
Col. 4, Line 57; "investment of female mold" should read ---investment or female mold---
Col. 12, Line 46; "components" should read ---Components---
Col. 14, Line 9-10; "(oxytetramethylene " should read --(oxytetramethylene)--
Col. 14, Line 16;"(oxypropylene " should read ---(oxypropylene)---

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*